(12) United States Patent
Denham

(10) Patent No.: US 10,987,125 B2
(45) Date of Patent: Apr. 27, 2021

(54) CAPSULE CUTTER

(71) Applicant: Biomet Sports Medicine, LLC, Warsaw, IN (US)

(72) Inventor: Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 214 days.

(21) Appl. No.: 15/372,955

(22) Filed: Dec. 8, 2016

(65) Prior Publication Data

US 2017/0172604 A1 Jun. 22, 2017

Related U.S. Application Data

(60) Provisional application No. 62/268,015, filed on Dec. 16, 2015.

(51) Int. Cl.
*A61B 17/3205* (2006.01)
*A61B 17/32* (2006.01)
(Continued)

(52) U.S. Cl.
CPC .......... *A61B 17/32053* (2013.01); *A61B 17/320016* (2013.01); *A61B 17/3468* (2013.01);
(Continued)

(58) Field of Classification Search
CPC ...... A61B 17/320783; A61B 17/32053; A61B 17/320016; A61B 2017/320052
See application file for complete search history.

(56) References Cited

U.S. PATENT DOCUMENTS 5,529,580 A * 6/1996 Kusunoki ........ A61B 17/32002
604/22
5,797,907 A * 8/1998 Clement ................ A61B 10/04
606/45

(Continued)

FOREIGN PATENT DOCUMENTS

DE 29521451 U1 5/1997
EP 2311394 A1 4/2011
EP 2666422 A1 11/2013

OTHER PUBLICATIONS

"European Application Serial No. 16204541.3, Response filed Apr. 20, 2018 to Office Action dated Sep. 22, 2017", 13 pgs.
(Continued)

*Primary Examiner* — Thomas McEvoy
(74) *Attorney, Agent, or Firm* — Schwegman Lundberg & Woessner, P.A.

(57) ABSTRACT

A system and method for cutting tissue within a synovial cavity, which includes a cannula and a blade assembly. The cannula can define an internal lumen and a cutting port for accessing the internal lumen. The blade assembly can include a blade and a blade shall extending from the blade. The blade can be inserted into the internal lumen of the cannula through an access port of the cannula such that the blade is proximate the cutting port. The blade shaft can be operated to move the blade within the internal lumen relative to the cutting port between a retracted position and a deployed position. The blade can be received within the internal lumen in the retracted position and positioned, at least partially, within the cutting port in the deployed position.

6 Claims, 5 Drawing Sheets

(51) Int. Cl.
  *A61B 17/34*  (2006.01)
  *A61B 90/00*  (2016.01)
  *A61B 17/00*  (2006.01)

(52) U.S. Cl.
  CPC ............. *A61B 17/320036* (2013.01); *A61B 2017/00393* (2013.01); *A61B 2017/00477* (2013.01); *A61B 2017/320052* (2013.01); *A61B 2090/08021* (2016.02)

(56) References Cited

U.S. PATENT DOCUMENTS

2010/0331883 A1* 12/2010 Schmitz ............. A61B 10/0275
  606/249
2011/0046652 A1  2/2011 Rehnke et al.

OTHER PUBLICATIONS

"European Application Serial No. 16204541.3, Extended European Search Report dated Sep. 22, 2017", 8 pgs.
"U.S. Appl. No. 15/372,955, Response filed Apr. 16, 2019 to Non Final Office Action dated Nov. 16, 2018", 9 pgs.

* cited by examiner

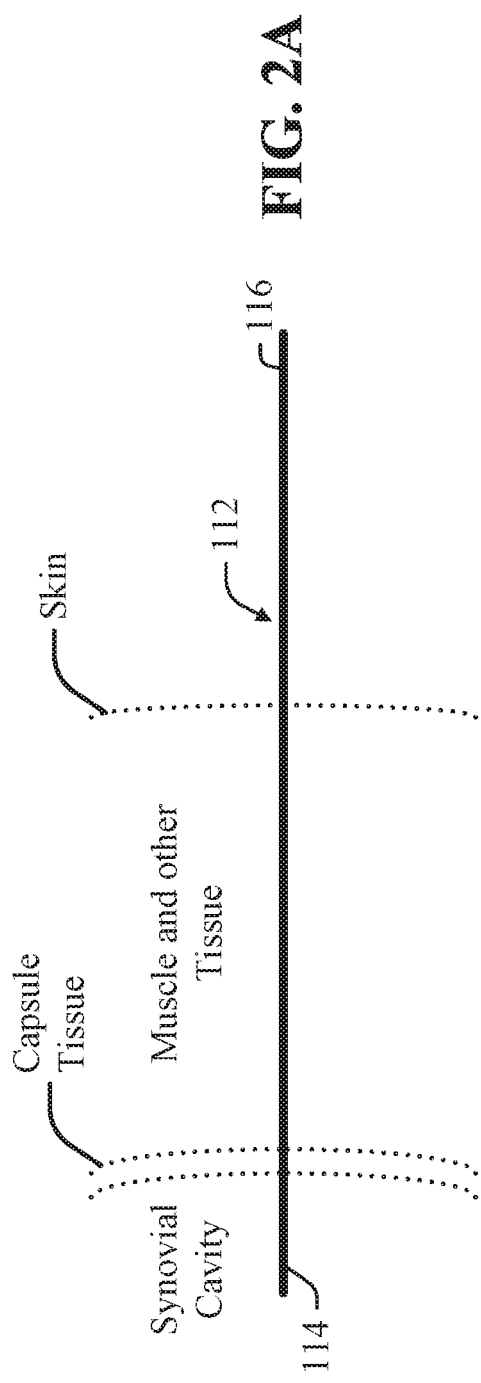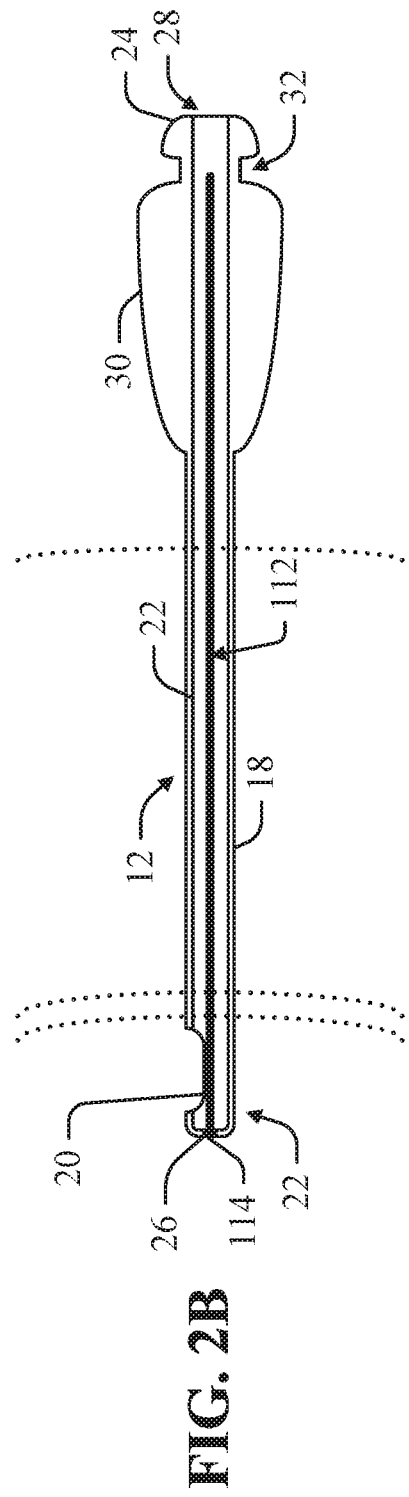

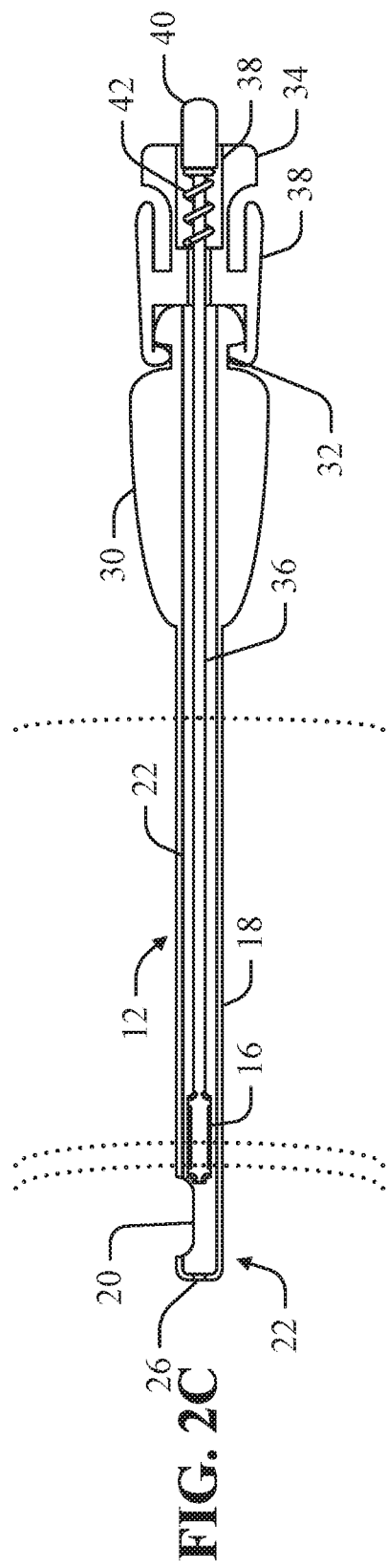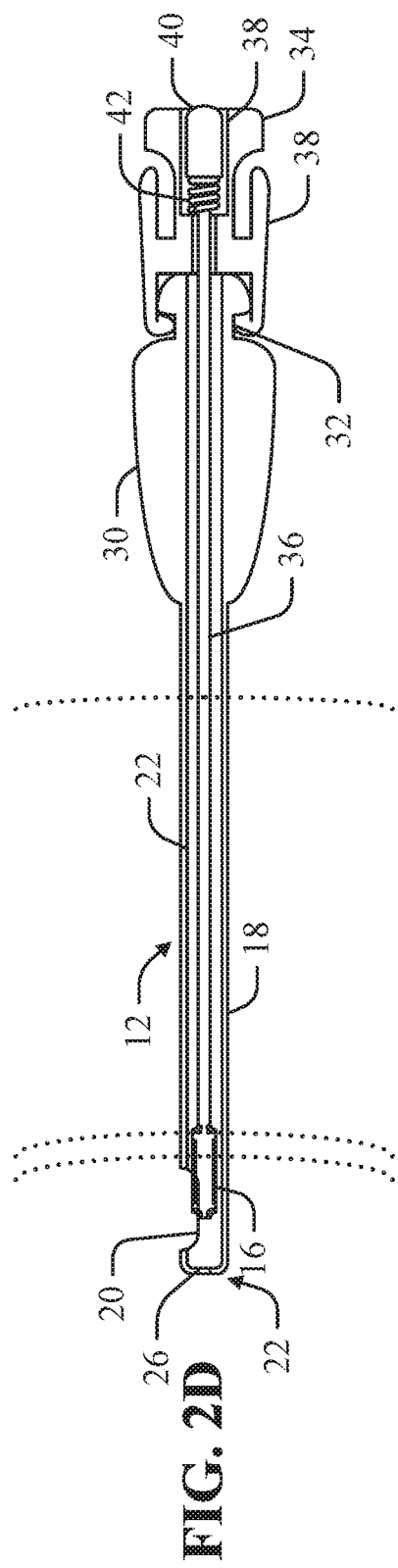

CAPSULE CUTTER

CLAIM OF PRIORITY

This patent application claims the benefit of priority, under 35 U.S.C. Section 119(e), to Gregory J. Denham U.S. Patent Application Ser. No. 62/268,015, entitled "CAPSULE CUTTER," filed on Dec. 16, 2015 (Attorney Docket No. 4394.E49PRV), which is hereby incorporated by reference herein in its entirety.

TECHNICAL FIELD

This document pertains generally, but not by way of limitation, to a system for and related methods of piercing an articular capsule.

BACKGROUND

Synovial joints have an articular capsule that surrounds the cartilage separating the bone ends and defines a synovial cavity that contains synovial fluid. The cartilage and other tissue within the synovial cavity can become damaged through overuse or injury requiring resection and removal of the damaged tissue. The damaged tissue can be removed by inserting a blade into the synovial cavity to resect the damaged tissue within the synovial cavity.

An arthroscopic procedure is frequently used to puncture the capsule tissue and provide an opening through which the blade can he inserted into the synovial cavity. The blade is typically set at an appropriate depth with an arthroscopic camera positioned within the synovial cavity. A switching stick or a Kirschner wire ("K-wire") is inserted through the exterior tissue and to the desired depth within the synovial cavity as visually confirmed by the arthroscopic camera. The switching stick can be used to guide a cannula inserted over the switching stick through the tissue wall into the synovial cavity. The switching stick can then be removed through the cannula and a blade can be inserted through the cannula, where the cannula protects the tissue wall of the synovial cavity from the blade as the blade is inserted within the synovial cavity. The cannula can be partially or entirely removed from the synovial cavity to unsheathe the cavity, which can be then maneuvered to resect the damaged tissue. The cannula can then be reinserted into the synovial cavity and the blade withdrawn through the cannula. After the blade is withdrawn, the switching stick can be reinserted into the cannula to guide removal of the cannula from the body.

A drawback of this approach is that the exposed blade can inadvertently damage healthy tissue by the fully exposed blade as the blade is maneuvered within the synovial cavity to cut the damaged tissue. Similarly, maneuvering of the cannula to unsheathe and sheathe the blade can cause unnecessary damage to the tissue wall. A related drawback is that the blade is often very thin to be passed through the cannula and can often break off during the resecting of damaged tissue. If the broken off portion of the blade cannot be retrieved through an arthroscopic procedure, a conventional invasive procedure that forms a larger opening the articular capsule could be required to retrieve the broken blade portion. Both the additional arthroscopic procedure and the conventional invasive procedure creates considerable risk for the patient and cause unnecessary damage to the healthy tissue.

Overview

The present inventors have recognized, among other things, that a problem to be solved can include safely delivering a blade to within a synovial cavity and minimizing risk of a broken or damaged blade. In an example, the present subject matter can provide a solution to this problem, such as by positioning the blade within an inner lumen of a cannula having a cutting port. The blade can be moved within the cannula between a deployed position in which the blade is positioned within the cutting port to permit cutting of tissue through the cutting port and a retracted position in which the blade is pulled away from the cutting port to prevent inadvertent cutting of tissue through the cutting port. The cutting port can be positioned in a radial wall of the cannula such that the cannula end is closed or partially closed thereby reducing the risk of a broken portion of the blade becoming lost within the synovial cavity. In at least one example, the closed or partially closed end of the cannula can shield the surrounding tissue from the blade preventing cutting of tissue by the blade except through the cutting port.

In an example, a method for cutting tissue within a synovial cavity can include inserting a proximal end of a guide element into the synovial cavity. The method can also include inserting a proximal end of a cannula into the synovial cavity over the guide element. The cannula can define an internal lumen extending from the proximal end and a distal end and a cutting port for accessing the internal lumen. The method can also include inserting a blade positioned on a blade shaft into the internal lumen through an access port such that the blade is positioned adjacent the cutting portion. The method can also include manipulating the blade shaft to move the blade between a retracted position and a deployed position. The blade is received entirely within the internal lumen in the retracted position and at least a portion of the blade is positioned within the cutting port in the deployed position.

In an example, a system for cutting tissue within a synovial cavity can include a cannula and a blade assembly. The cannula can define an internal lumen extending from a proximal end and a distal end and can also define a cutting port for accessing the internal lumen. The blade assembly can include a blade and a blade shaft extending from the blade. The blade can be inserted into the internal lumen of the cannula through an access port in the distal end of the cannula such that the blade is proximate the cutting port. The blade shaft can be operated to move the blade within the internal lumen relative to the cutting port between a retracted position and a deployed position. The blade can be received within the internal lumen in the retracted position and positioned within the cutting port in the deployed position.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2A is a schematic view of insertion of a switching stick into a synovial cavity according to an example of the present disclosure.

FIG. 2B is a schematic view of insertion of a cannula assembly according to an example of the present disclosure over the switching stick depicted in FIG. 2A.

FIG. 2C is a schematic view of insertion of a blade assembly according to an example of the present disclosure within the cannula assembly depicted in FIG. 2B such that the blade is positioned in the retracted position.

FIG. 2D is a schematic view of actuation of the blade assembly to deploy a blade through a cutting port of the cannula assembly according to an example of the present disclosure.

DETAILED DESCRIPTION

Figure 1:
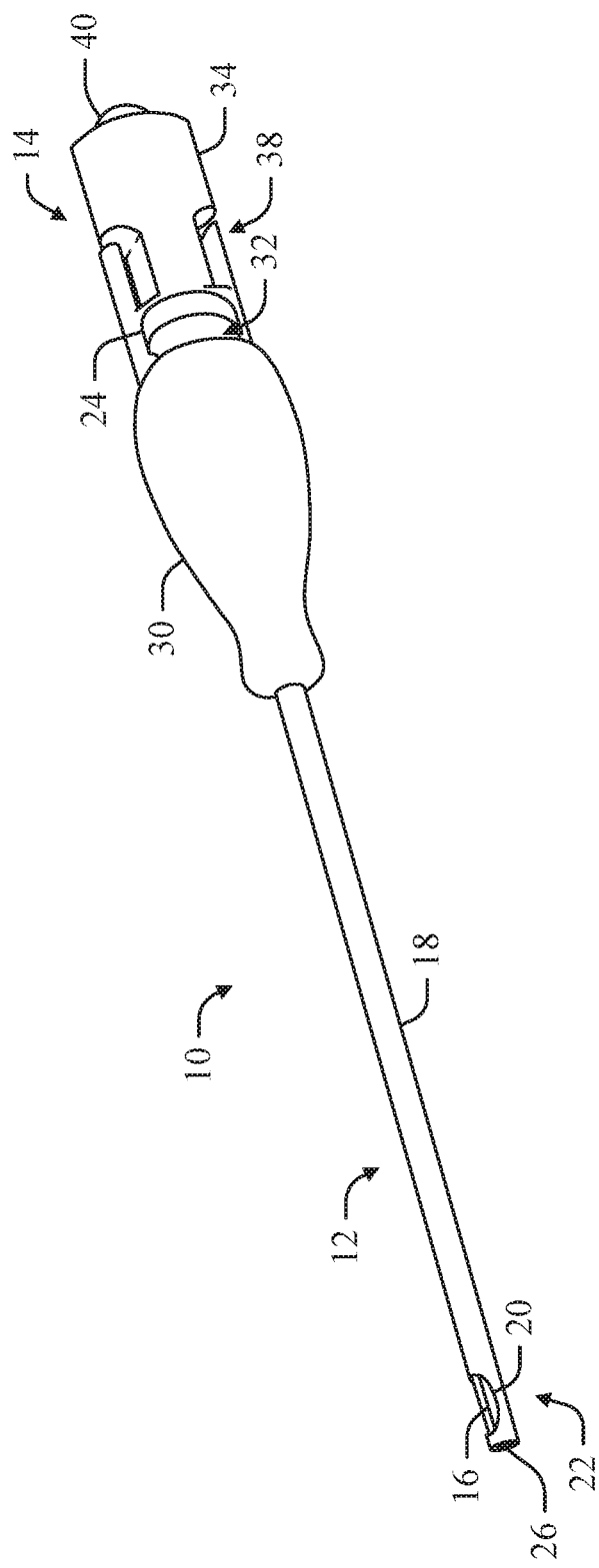
FIG. 1 is a perspective view of a capsule cutter system according to an example of the present disclosure.

As depicted in FIG. 1, a capsule cutter 10, according to an example of the present disclosure, can include a cannula assembly 12 and a blade assembly 14 having at least one blade 16 (referred to as "the blade 16" or "each blade 16" herein). The blade assembly 14 can be partially inserted into the cannula assembly 12 such that each blade 16 can be positioned within a cannula 18 of the cannula assembly. The blade assembly 14 can be actuated to move each blade 16 between a deployed position and a retracted position. In the deployed position, each blade 16 can be positioned within a cutting port 20 of the cannula 18 such that tissue can pass through the cutting port 20 for cutting with the corresponding blade 16. In the retracted position, each blade 16 can be positioned away from the cutting port 20 to avoid cutting any tissue that enters the cutting port 20. In at least one example, the blade assembly 14 can be configured such that each blade 16 can be initially positioned at the retracted position when the blade assembly 14 can be inserted into the cannula assembly 12.

As depicted in FIGS. 1, 2B-2D, and 3, the cannula assembly 12 can include a cannula 18 having a proximal end 22 and a distal end 24 and defining at least one internal lumen 22 extending from the proximal end 22 to the distal end 24. The cannula 18 can define at least one cutting port 20 for accessing the internal lumen 22. In an example, the cutting port 20 can be positioned on a side wall of the cannula 18 between the proximal end 22 and the distal end 24. In at least one example, the cutting port 20 can be positioned on a side wall of the cannula 18 proximal the proximal end 22. The cannula 18 can include a guide port 26 positioned at the proximal end 22 and defining a proximal opening of the internal lumen 22. In an example, the guide port 26 can be aligned with a longitudinal axis A-A defined by the internal lumen 22 of the cannula 18. The cannula 18 can include an access port 28 proximal the distal end 24. In an example, the access port 28 can be aligned with the longitudinal axis A-A.

As depicted in FIGS. 1, 2B-2D, and 3, the cannula assembly 12 can include a handle portion 30 positioned proximal the distal end 24 of the cannula assembly 12. In an example, the handle portion 30 can define the access port 28 of the internal lumen 22. The handle portion 30 can be gripped by an operator for positioning and reorienting the cannula 18. In an example, the handle portion 30 can define an engagement feature 32 for attachment of the blade assembly 14 to the distal end 24 of the cannula assembly 12.

As depicted in FIGS. 2C-2D, the blade assembly 14 can include the blade 16, a base 34, and a shaft 36 extending between the blade 16 and the base 34. The blade 16 can be inserted into the internal lumen 22 through the access port 28. In an example, the shaft 36 can be sized such that the blade 16 can be proximate the cutting port 20 when the blade 16 can be inserted through the access port 28 and the base 34 engages the cannula assembly 12. In an example, the base 34 can include a releasable engagement feature 38 corresponding to the engagement feature 32 of the handle port 30 to releasably attach the blade assembly 14 to the cannula assembly 12 when the blade 16 can be inserted into the internal lumen 22.

Figure 3:
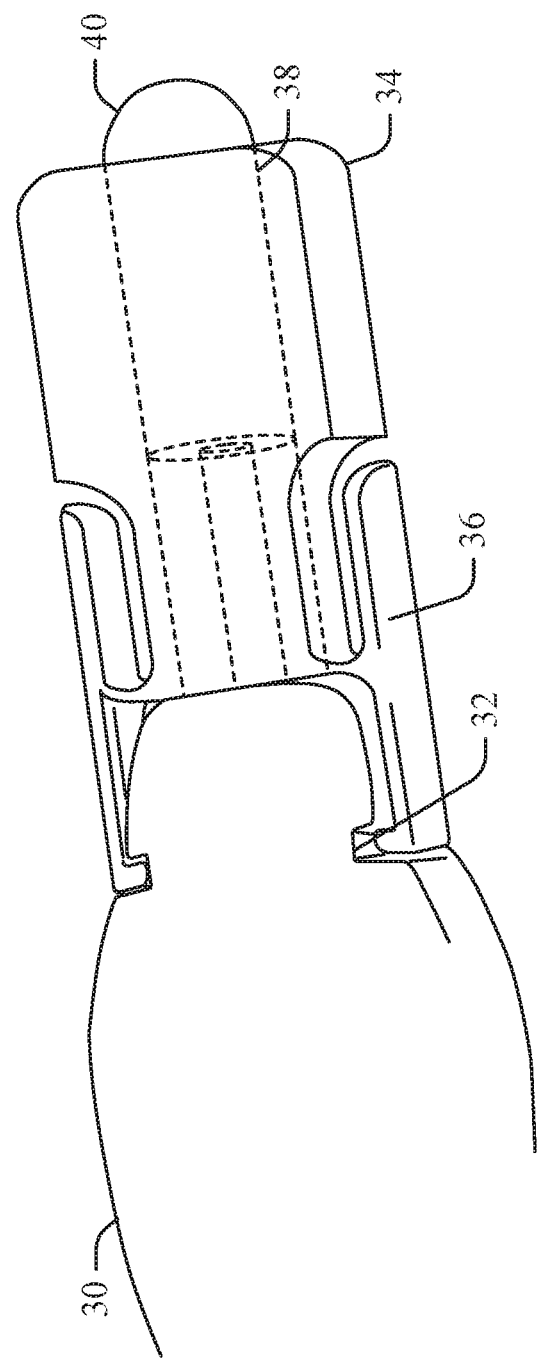
FIG. 3 is a partial cross-sectional view of attachment of a blade assembly to a cannula assembly according to an example of the present disclosure.
Figure 4:
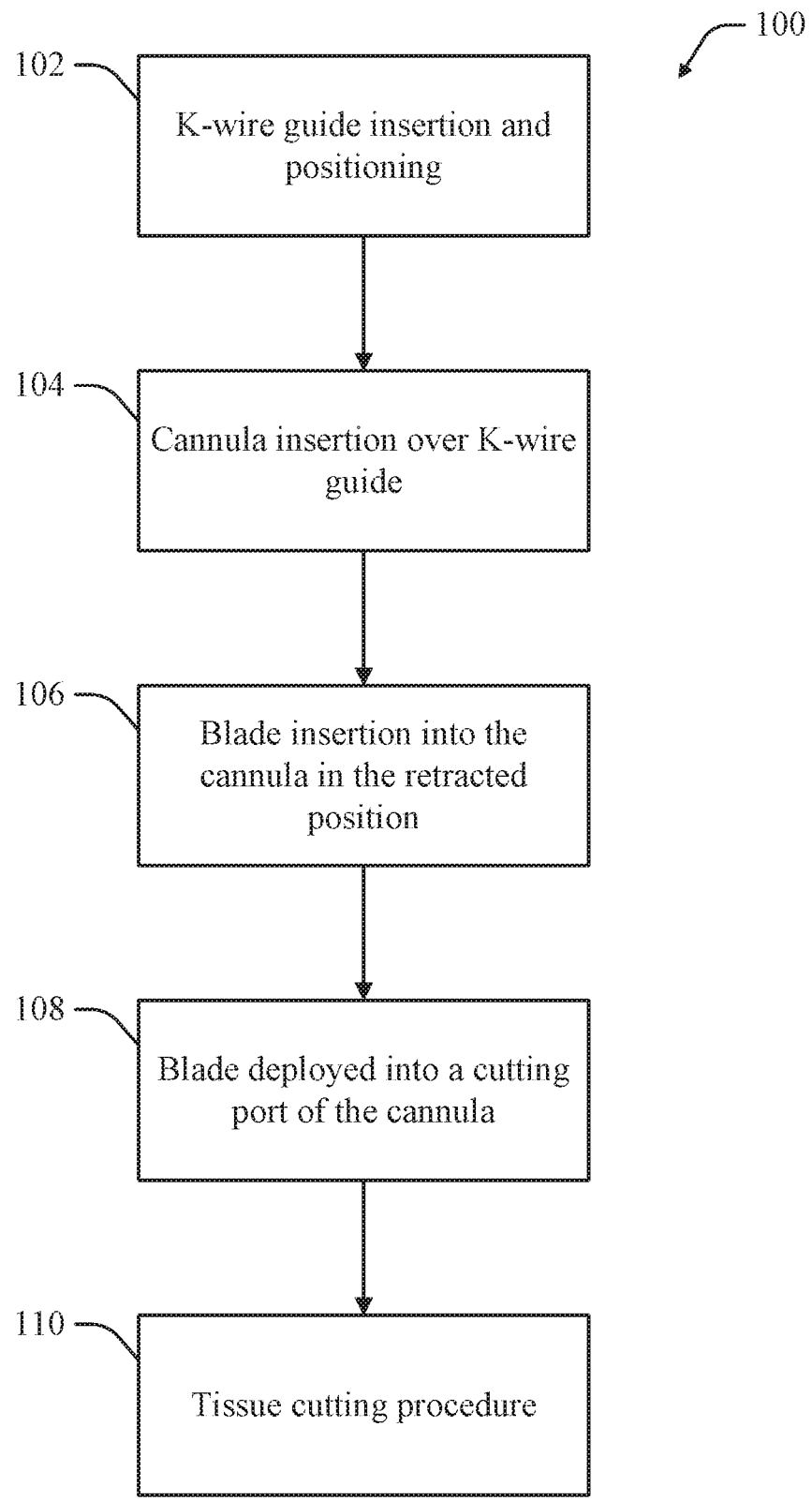
FIG. 4 is a diagram of a method of transporting a blade safely into a synovial cavity and deploying the blade within the synovial cavity according to an example of the present disclosure.

As depicted in FIGS. 2C-2D and 3, in an example, the shaft 36 can be slidably received within a channel 38 defined by the base 34 such that the shaft 36 can be slidable relative to the base 34 to move the blade 16 between a retracted position and a deployed position. As depicted in FIG. 2C, in the retracted position, the blade 16 can be moved away from the cutting port 20 such that the blade 16 can be primarily received within the internal lumen 22. In this configuration, the cannula 18 protects the surrounding tissue from the blade 16. As depicted in FIG. 2D, in the deployed position, the blade 16 can be moved into the cutting port 20 such that a portion of the blade 16 can be exposed through the cutting port 20.

In an example, the shaft 36 can include a button 40 that can be manipulated to move the blade 16 between the retracted and deployed positions. In at least one example, the base 34 can include a spring 42 positioned within the channel 38 to bias the shaft 36 toward the retracted position. In this configuration, the blade assembly 14 can be attached to the cannula assembly 12 and the blade 16 inserted into the internal lumen 22 such that the blade 16 can be initially positioned in the retracted position. Upon manipulation by the operator, the blade 16 can be moved to the deployed position in order to position the blade 16 for cutting.

As depicted in FIGS. 2A-2D and 4, a method 100 for cutting tissue within a synovial cavity can comprise guide insertion and positioning 102; cannula insertion over guide 104; blade insertion into cannula 106; blade deployment into cutting portion of the cannula 108; and tissue cutting procedure 110.

As depicted in FIG. 2A, the guide insertion and positioning 102 can include insertion of a K-wire 112, switching stick or other guide element into the synovial cavity. The K-wire 112 can be inserted such that a proximal end 114 of the K-wire 112 can be positioned to a pre-determined depth within the synovial cavity. As illustrated in FIG. 2B, in an example, the pre-determined depth can be sufficient to such that the cutting port 20 is fully within the synovial cavity when the cannula 18 can be inserted into the synovial cavity along the K-wire 112 and such that the proximal end 22 of the cannula 18 approximate the proximal end 114 of the K-wire 112.

As depicted in FIG. 2B, cannula insertion over guide 104 can include feeding a distal end 116 of the K-wire 112 into the guide port 26 of the cannula 18 and inserting the cannula 18 through the tissue along the K-wire 112. In this configuration, the longitudinal axis A-A of the cannula 18 is generally parallel to the K-wire 112 as the cannula 18 is inserted through the tissue. In an example, the cannula 18 can be inserted such that the proximal end 22 of the cannula 18 approximate the proximal end 114 of the K-wire 112.

As depicted in FIG. 2C, the blade insertion into cannula 106 can include insertion of the blade 16 and at least a portion of the blade shaft 36 of blade assembly 14 through the access port 28 in the handle assembly 12. In an example, the releasable attachment feature 38 of the blade assembly 14 can be engaged to the attachment feature 32 to attach the blade assembly 14 to the handle assembly 12. In an example, the blade shaft 36 can be sized such that the blade 16 can be initially positioned in the retracted position when the blade assembly 14 can be attached to the handle assembly 12 as depicted in FIG. 2C. In at least one example, the K-wire 112 can be removed from the tissue by drawing the K-wire 112 from the cannula 18 through the access port 28 prior to the insertion of the blade assembly 14.

As depicted in FIG. 2D, the blade deployment 108 can include manipulating the button 40 of the blade shaft 36 to move the blade 16 axially such that the blade 16 can be moved into the deployed position and positioned within the cutting port 20. In an example, the spring 42 can be compressed as the blade 16 is moved into the deployed position such that the spring 42 biases the blade 16 toward the retracted position when the blade 16 is released.

In the tissue cutting procedure 110, the handle 30 can be manipulated to move the proximal end 22 of the cannula 18 and the blade 16 contained therein to position tissue within the cutting port 20 for cutting with the blade 16. In an example, the button 40 can remain depressed while the tissue is being cut and released to retract the blade 16 when tissue cutting is completed.

VARIOUS NOTES & EXAMPLES

Example 1 can include subject matter, such as can include a method for cutting tissue within a synovial cavity, including inserting an inserted end of a guide element 112 into the synovial cavity. The method can include inserting a proximal end 22 of a cannula 18 into the synovial cavity over the guide element 112. The cannula 18 defines an internal lumen 22 extending from the proximal end 22 and a distal end 24 and a cutting port 20 for accessing the internal lumen 22. The method can include inserting a blade 16 positioned on a blade shaft 36 into the internal lumen 22 through an access port 28 such that the blade 16 can be positioned adjacent the cutting port 20. The method can also include manipulating the blade shaft 36 to move the blade 16 between a retracted position and a deployed position. The blade 16 can be received entirely within the internal lumen 22 in the retracted position and at least a portion of the blade 16 can be positioned within the cutting port 20 in the deployed position.

Example 2 can include, or can optionally be combined with the subject matter of Example 1, to optionally include that the guide element 112 can comprise at least one of K-wire and a switching stick.

Example 3 can include, or can optionally be combined with the subject matter of one or any combination of Examples 1 or 2 to optionally include withdrawing the guide element 112 from the synovial cavity and the internal lumen 22 of the cannula 18 through the access port 28 in the cannula 18.

Example 4 can include, or can optionally be combined with the subject matter of Example 3, to optionally include that the guide element 112 can be withdrawn from the internal lumen 22 of the cannula 18 prior to insertion of the blade 16.

Example 5 can include, or can optionally be combined with the subject matter of one or any combination of any one of the preceding claims to optionally include that the cannula 18 defines a guide port 26 at the proximal end 22 of the cannula 18. The guide element 112 can be inserted into the guide port 26 to align the cannula 18 with the guide element 112 as the cannula 18 can be inserted over the guide element 112.

Example 6 can include, or can optionally be combined with the subject matter of one or any combination of any one of the preceding claims to optionally include that the cannula 18 further includes an engagement feature 32.

Example 7 can include, or can optionally be combined with the subject matter of Example 6, to optionally include that the blade shaft 36 includes a base 34 including a releasable engagement feature 38. The releasable engagement feature 38 can be engaged to the engagement feature 32 when the blade 16 is inserted into the internal lumen 22 to prevent removal of the blade 16 from the internal lumen 22 of the cannula 18.

Example 8 can include, or can optionally be combined with the subject matter of Example 7, to optionally include manipulating the releasable engagement feature 38 to disengage the blade 16 from the cannula 18; and drawing the blade 16 from the cannula 18 through the access port 28.

Example 9 can include, or can optionally be combined with the subject matter of one or any combination of any one of the preceding claims to optionally include depressing a button attached to the blade shaft 36 to move the blade 16 into the deployed position.

Example 10 can include, or can optionally be combined with the subject matter of Example 9, to optionally include that the base 34 includes a spring 42 compressible as the blade 16 can be moved into the deployed position to bias the blade 16 toward the retracted position.

Example 11 can include, or can optionally be combined with the subject matter of one or any combination of Examples 9 or 10, to optionally include manipulating the cannula 18 to maneuver the proximal end 22 and cutting port 20 of the cannula 18 to draw tissue into the cutting port 20.

Example 12 can include, or can optionally be combined with the subject matter of Example 11, to optionally include that the button 40 can be depressed as the tissue can be drawn into the cutting port 20 to cut the tissue with the blade 16.

Example 13 can include, or can optionally be combined with the subject matter of Example 11, to optionally include that the button 40 can depressed after the tissue can be drawn into the cutting port 20 to move the blade 16 into the deployed position and cut tissue drawn into the cutting port 20.

Example 14 can include subject matter, such as can include a system for cutting tissue within a synovial cavity that can include a cannula 18 and a blade assembly. The cannula 18 can define an internal lumen 22 extending from a proximal end 22 and a distal end 24 and defining a cutting port 20 for accessing the internal lumen 22. The blade assembly can include a blade 16 and a blade shaft 36 extending from the blade 16. The blade 16 can inserted into the internal lumen 22 of the cannula 18 through an access port 28 in the distal end 24 of the cannula 18 such that the blade 16 can be proximate the cutting port 20. The blade shaft 36 can be operated to move the blade 16 within the internal lumen 22 relative to the cutting port 20 between a retracted position and a deployed position. The blade 16 can be received within the internal lumen 22 in the retracted position. The blade 16 can be positioned within the cutting port 20 in the deployed position.

Example 15 can include, or can optionally be combined with the subject matter of Example 14, to optionally include that the cutting port 20 can be positioned in a radial side wall of the cannula 18.

Example 16 can include, or can optionally be combined with the subject matter of one or any combination of Examples 14 or 15 to optionally include that the proximal end 22 can be closed.

Example 17 can include, or can optionally be combined with the subject matter of one or any combination of Examples 14-16 to optionally include that the cannula 18 defines a guide port 26 in the proximal end 22 for receiving a guide element 112.

Example 18 can include, or can optionally be combined with the subject matter of Example 17, to optionally include that the guide element 112 can comprise at least one of K-wire and a switching stick.

Example 19 can include, or can optionally be combined with the subject matter of one or any combination of Examples 17 or 18 to optionally include that the guide element 112 is removable through the access port 28 in the distal end 24 of the cannula 18.

Example 20 can include, or can optionally be combined with the subject matter of one or any combination of Examples 17-19 to optionally include that the wide element 112 can be withdrawn from the internal lumen 22 of the cannula 18 prior to insertion of the blade 16.

Example 21 can include, or can optionally be combined with the subject matter of one or any combination of Examples 17-20 to optionally include that the cannula 18 further includes an engagement feature 32.

Example 22 can include, or can optionally be combined with the subject matter of Example 21, to optionally include a base 34 including a releasable engagement feature 38. The releasable engagement feature 38 can be engaged to the engagement feature 32 when the blade 16 can be inserted into the internal lumen 22 to prevent removal of the blade 16 from the internal lumen 22 of the cannula 18.

Example 23 can include, or can optionally be combined with the subject matter of one or any combination of Examples 17-22 to optionally include that the blade shaft 36 can further include a button operable to move the blade 16 into the deployed position via the blade shaft 36.

Example 24 can include, or can optionally be combined with the subject matter of Example 23, to optionally include that the base 34 can further include a spring 42 compressible as the blade 16 can be moved into the deployed position to bias the blade 16 toward the retracted position.

Example 25 can include, or can optionally be combined with the subject matter of one or any combination of Examples 23 or 24 to optionally include manipulating the cannula 18 to maneuver the proximal end 22 and cutting port 20 of the cannula 18 to draw tissue into the cutting port 20.

Example 26 can include, or can optionally be combined with the subject matter of Example 25, to optionally include that the button 40 can be depressed as the tissue is drawn into the cutting port 20 to cut the tissue with the blade 16.

Example 27 can include, or can optionally be combined with the subject matter of Example 25, to optionally include that the button 40 can be depressed after the tissue is drawn into the cutting port 20 to move the blade 16 into the deployed position and cut tissue drawn into the cutting port 20.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A system for cutting tissue within a synovial cavity, comprising:
   a cannula including an engagement feature, the cannula defining:
      an internal lumen extending from a proximal end to a distal end,
      a cutting port in a wall of the cannula for accessing the internal lumen, wherein the cannula is cylindrical and the cutting port is formed through a radial sidewall of the cylindrical cannula,
      a guide port in the proximal end for receiving a guide element, and
      an access port in the distal end of the cannula, wherein the guide element is removable through the access port; and
   a blade assembly including a blade and a blade shaft extending from the blade, wherein the blade is insertable into the internal lumen of the cannula through the access port in the distal end of the cannula such that the blade is proximate the cutting port, wherein the blade shaft is operable to move the blade within the internal lumen relative to the cutting port between a retracted position and a deployed position, the blade assembly including a base including a releasable engagement feature, wherein the releasable engagement feature is engageable to the engagement feature of the cannula when the blade is inserted into the internal lumen to prevent removal of the blade form the internal lumen of the cannula;
   wherein the blade is received within the internal lumen in the retracted position and the blade is positioned within the cutting port in the deployed position
   wherein the blade is configured such that a sharp edge of the blade faces the cutting port in the deployed position.

2. The system of claim 1, wherein the guide element can comprise at least one of a K-wire and a switching stick.

3. The system of claim 1, wherein the guide element is withdrawn from the internal lumen of the cannula prior to insertion of the blade.

4. The system of claim 1, wherein the blade shaft further comprises:
   a button operable to move the blade into the deployed position via the blade shaft,
   wherein the base further comprises:
   a spring compressible as the blade is moved into the deployed position to bias the blade toward the retracted position.

5. The system of claim 4, wherein the cannula can be manipulated to maneuver the proximal end and cutting port of the cannula to draw tissue into the cutting port;
   wherein the button is configured to be depressed as the tissue is drawn into the cutting port to cut the tissue with the blade.

6. The system of claim 5, wherein the button is configured to be depressed after the tissue is drawn into the cutting port to move the blade into the deployed position and cut tissue drawn into the cutting port.

* * * * *